United States Patent [19]

Buytaert et al.

[11] Patent Number: 5,546,473
[45] Date of Patent: Aug. 13, 1996

[54] FAST INTERACTIVE OFF-LINE PROCESSING METHOD FOR RADIOGRAPHIC IMAGES

[75] Inventors: Tom G. Buytaert, Kontich; Stefan C. Van de Velde, Zaventem; Pieter P. Vuylsteke, Mortsel, all of Belgium

[73] Assignee: AGFA-Gevaert, Mortsel, Belgium

[21] Appl. No.: 83,914

[22] Filed: Jun. 28, 1993

[30] Foreign Application Priority Data

Feb. 11, 1993 [EP] European Pat. Off. .............. 93200374

[51] Int. Cl.⁶ .................................................. G06K 9/00
[52] U.S. Cl. ............................................ 382/132; 382/299
[58] Field of Search ........................... 382/6, 54, 128, 382/132, 299, 300, 302, 298; 342/179; 378/87, 98.12

[56] References Cited

U.S. PATENT DOCUMENTS

| | | | |
|---|---|---|---|
| 4,716,414 | 12/1987 | Luttrell | 342/179 |
| 4,845,762 | 7/1989 | Higashi | 382/6 |
| 4,924,521 | 5/1990 | Dinan | 382/54 |
| 5,153,936 | 10/1992 | Morris | 382/47 |

*Primary Examiner*—Yon J. Couso
*Attorney, Agent, or Firm*—Richard J. Birch

[57] ABSTRACT

A fast off-line image processing method for radiographic images is disclosed wherein an image is decomposed into detail image and multiple resolution levels and a residual image, detail images are modified up to a preset resolution level and a processed image is reconstructed by means of the modified detail images and the residual image. Interactive processing is performed with different parameter settings.

4 Claims, 5 Drawing Sheets

| 0.0025 | 0.0125 | 0.02 | 0.0125 | 0.0025 |
|--------|--------|------|--------|--------|
| 0.0125 | 0.0625 | 0.1  | 0.0625 | 0.0125 |
| 0.02   | 0.1    | 0.16 | 0.1    | 0.02   |
| 0.0125 | 0.0625 | 0.1  | 0.0625 | 0.0125 |
| 0.0025 | 0.0125 | 0.02 | 0.0125 | 0.0025 |

FAST INTERACTIVE OFF-LINE PROCESSING METHOD FOR RADIOGRAPHIC IMAGES

FIELD OF THE INVENTION

The present invention is in the field of digital radiography and more specifically relates to image processing and display of digital radiographic images on a workstation.

BACKGROUND OF THE INVENTION

In the field of digital radiography a wide variety of image acquisition techniques have been developed rendering a digital representation of a radiographic image.

Among such techniques are computerised tomography, nuclear magnetic resonance, ultrasound detection, detection of a radiation image by means of a CCD sensor or a video camera, radiographic film scanning etc.

In still another technique a radiation image, for example an x-ray image of an object, is stored in a screen comprising a photostimulable phosphor such as one of the phosphors described in European patent publication 503 702 published on 16.09.92. The technique for reading out the stored radiation image consists of scanning the screen with stimulating radiation, such as laser light of the appropriate wavelength, detecting the light emitted upon stimulation and converting the emitted light into an electric representation for example by means of a photomultiplier and finally digitizing the signal.

One of the benefits of a digital radiographic system resides in the possibility of processing the digital image representation before display or hard copy recording. The term "processing" in this context means any kind of image-processing such as noise filtering, contrast enhancement, data compression etc.

The processing can be performed on-line or off-line, the present invention specifically relates to off-line processing on a graphical work station.

The procedure commonly followed on a workstation is as follows. The image signal acquired by an image acquisition device as described above is stored in memory and retrieved from that memory at the time of off-line processing, the actual processing is then performed and the processed image is applied to a monitor for display and evaluation. The processing takes into account processing parameters that are either associated to the image in the very beginning of the process, so for example in an image identification phase proceeding the read-out phase in case of a radiation image stored in a photostimulable phosphor screen. Alternatively processing parameters can be entered by the operator via the console of the work station or preset processing procedures can be applied. Processing on a work station is frequently performed interactively. Then the original image signal is processed during successive processing cycles with different parameter settings and is each time evaluated and reprocessed until the obtained result meets the objectives as to image quality or diagnostic requirement.

A digital radiographic image is commonly represented by about 10 MB digital data. The computation time required for processing such a amount of data may extend to orders of minutes per processing cycle.

In case of interactive processing, comprising multiple processing cycles, the display of successively processed images (with different processing settings) is each time interrupted by a relatively long wait cycle and the total processing procedure (depending on the number of interactive processing cycles) may be very long.

OBJECTS OF THE INVENTION

It is an object of the present invention to provide a method of obtaining on a work station in a fast way a processed image with an image quality that is adequate for diagnostic evaluation.

It is a further object to provide such a method which permits application in an interactive system wherein radiographic image evaluation comprises several processing cycles with amended processing parameters.

It is still a further object to provide such a method in a system for reading radiographic image stored in a photostimulable phosphor screen.

STATEMENT OF THE INVENTION

The objects of the present invention are achieved by a method of processing a digital signal representation of a radiographic image comprising the steps of:

1)-transforming said image into a decomposed image comprising a sequence of detail images at multiple resolution levels and a residual image, 2)-storing said detail images and said residual image, 3)-retrieving said decomposed image up to a predetermined resolution level from said memory, 4)-processing said retrieved decomposed image taking into account a set of processing parameters, 5)-reconstructing a processed image by applying the inverse of the decomposition transformation to the images processed in step 4 and the residual image, 6)-displaying said processed image and evaluating said processed image, 7)-in dependence on the result of said evaluation amending processing parameters and repeating method steps 3 to 6.

In the description hereinbelow interactions performed on an image or on a so-called detail image are to be interpreted as meaning interactions performed on the digital signal representation thereof.

Once the displayed image satisfies the operator, the above image processing method can be completed by the steps of retrieving all detail images and a residual image from said memory and performing processing of all retrieved detail images taking into account a set of parameters, performing reconstruction of the processed image by applying the inverse of the decomposition transformation, outputting the reconstructed image.

Evidently the set of parameters that is preferably taken into account in the above additional processing step of the entire image is the set that led to a satisfactory evaluation.

Preferably optimal parameters providing a processed image that satisfies the operator are stored in a database and are retrieved to be applied for reproduction of a processed image.

These additional steps provide that after evaluation of the reconstructed partially processed image (namely processed up to a predetermined resolution level) on the monitor of the work station, processing of the entire image incorporating every resolution level can be ordered. This final processing can eventually be performed remote for example on a dedicated fast-working processor.

The finally processed image can then be transferred to an output recorder for hard copy recording such as a laser printer or a thermal printer (for example a thermal sublimation printer).

Alternatively or additionally the processed image can be sent to a long term mass storage device such as an optical disc for archival purposes.

The predetermined resolution level can be set so that it matches with the resolution of the monitor screen or is smaller than said resolution. The set resolution level needs to render a processed image with a resolution that is adequate for preliminary evaluation on the monitor screen.

The method of the present invention is advantageous and meets the enumerated objectives by limiting the retrieval and processing to image components (detail images and residual image) up to a predetermined resolution level.

The present invention provides that the time consuming image decomposition operation is only performed once and that the result hereof can be retrieved at any time for any kind of processing.

In this way a high quality image with a resolution that matches that of the monitor screen is obtained with as less as possible of computational effort.

The evaluation of a processed image is performed on the basis of a partially modified and partially reconstructed image since only part of the components of the decomposition process are taken into account. This procedure enhances the speed of operation and still provides an adequate tool for evaluation of the image quality and the diagnostic requirements.

Still the modification and reconstruction of the entire image which, due to the large number of pixels involved, is computationally expensive can be postponed until a satisfactory processing result is obtained on the subset of detail images.

Several examples of a decomposition procedure of an original image signal into a sequence of detail images and a residual image are described in our European application 91202079.9 filed on Jul. 30, 1992 and in U.S. Ser. No. 07/924,905 now U.S. Pat. No. 5,350,914.

In one embodiment of the signal processing method, the multiresolution representation obtained after decomposition has a pyramidal structure such that the resolution level of the detail images differs by a factor of 2, and the detail images at each resolution level are calculated by filtering the original image with the difference of two low-pass filters and by subsampling the resulting image by a factor 2.

The used filter preferably has a two dimensional Gaussian distribution.

Pyramidal image decomposition is preferred over alternative methods such as simple subsampling because the alternative methods induce frequency related patterns (line structures) referred to as "aliasing".

The processing performed on the decomposed image comprises a modification of pixel values of the detail images into which the image has been decomposed images to yield pixel values of a set of modified detail images.

In one embodiment, this modification is performed to enhance the image contrast and is performed by applying at least one non-linear monotonically increasing odd mapping function with a slope that gradually decreases with increasing argument values.

Alternative processing steps such as a noise suppression processing described in our copending European application number 92201802.3 filed Jun. 19, 1992, alternative contrast enhancement procedures, grey scale transforms, and other algorithms that optimize the diagnostic quality of an image, processing affecting the image orientation etc. may be performed.

Finally a processed image is computed by applying a reconstruction algorithm that performs the inverse transformation of the decomposition transformation to the residual image and the modified detail images. The above mentioned European application 91202079.9 filed 91.07.30 and U.S. Ser. No. 07/924,905 now U.S. Pat. No. 5,350,914 describes suitable reconstruction algorithms.

In one embodiment the digital image signal is obtained by reading a radiographic image that had been stored in a photostimulable phosphor screen by scanning said screen with stimulating radiation, detecting the light emitted upon stimulation and converting said light into a digital image signal.

In an alternative embodiment the digital signal is obtained by scanning a radiographic film with light and detecting the image-wise modulated eflected or transmitted light.

However, the invention is not limited to these acquisistion systems, alternatives may be envisoned.

Preferably the decomposition is performed in a processing section part of the read-out apparatus, the decomposed image is then transferred across a digital communication channel, such as a LAN (local area network) to a workstation where it is stored in a storage device for future processing.

This is advantageous since the decomposition is already required if online processing is performed on a decomposed image.

Processing parameters or an identifier of a set of stored processing parameters or processing procedure can be associated with the image prior to read out of the screen or can be fed to the workstation or amended via the console hereof.

The invention further provides an apparatus for carrying out the method of the present invention.

The apparatus generally comprises
- an image acquisition section-rendering a digital signal representation of a radiographic image,
- means for decomposing said digital signal representation into detail images at multiple resolution levels and a residual image,
- means for interfacing said acquisition section with said workstation,
- a workstation comprising
  - means for storing said detail images and said residual image,
  - a graphical user interface for selecting different processing modes,
  - means for controlling retrieval of detail images from said storage means up to a preset resolution level,
  - means for modifying said retrieved detail images according to said selected mode,
  - means for computing a reconstructed processed image by applying a reconstruction algorithm to the retrieved residual image and the retrieved and modified detail images, the reconstruction algorithm being such that if it were applied to the residual image and all detail images without modification, then said original image or a close approximation thereof would be obtained,
  - means for displaying a reconstructed image.

The processing modes are in a preferred embodiment preprogrammed processing algorithms with different sets of processing parameters that are stored in advance in a processing means and that can be retrieved by selection via the graphic user interface. The processing parameters can for example be linked to a specific radiologic examination type.

The apparatus may be equipped with a database for storing an optimal processing mode so that the processing may be repeated using the stored processing conditions.

The apparatus may additionally comprise means for controlling retrieval of all detail images and a residual image and means for controlling said processing and reconstruction on all retrieved detail images and the residual image.

In a preferred embodiment the acquisition section generally comprises means for scanning a photostimulable phosphor screen with stimulating irradiation, means for detecting the light emitted upon stimulation and means for converting the detected light into a signal representation.

Particular aspects of the present invention as well as preferred embodiments thereof will be illustrated by means of the following drawings.

FIG. 4 is an example of a filter used in the decomposition procedure.

Figure 1:
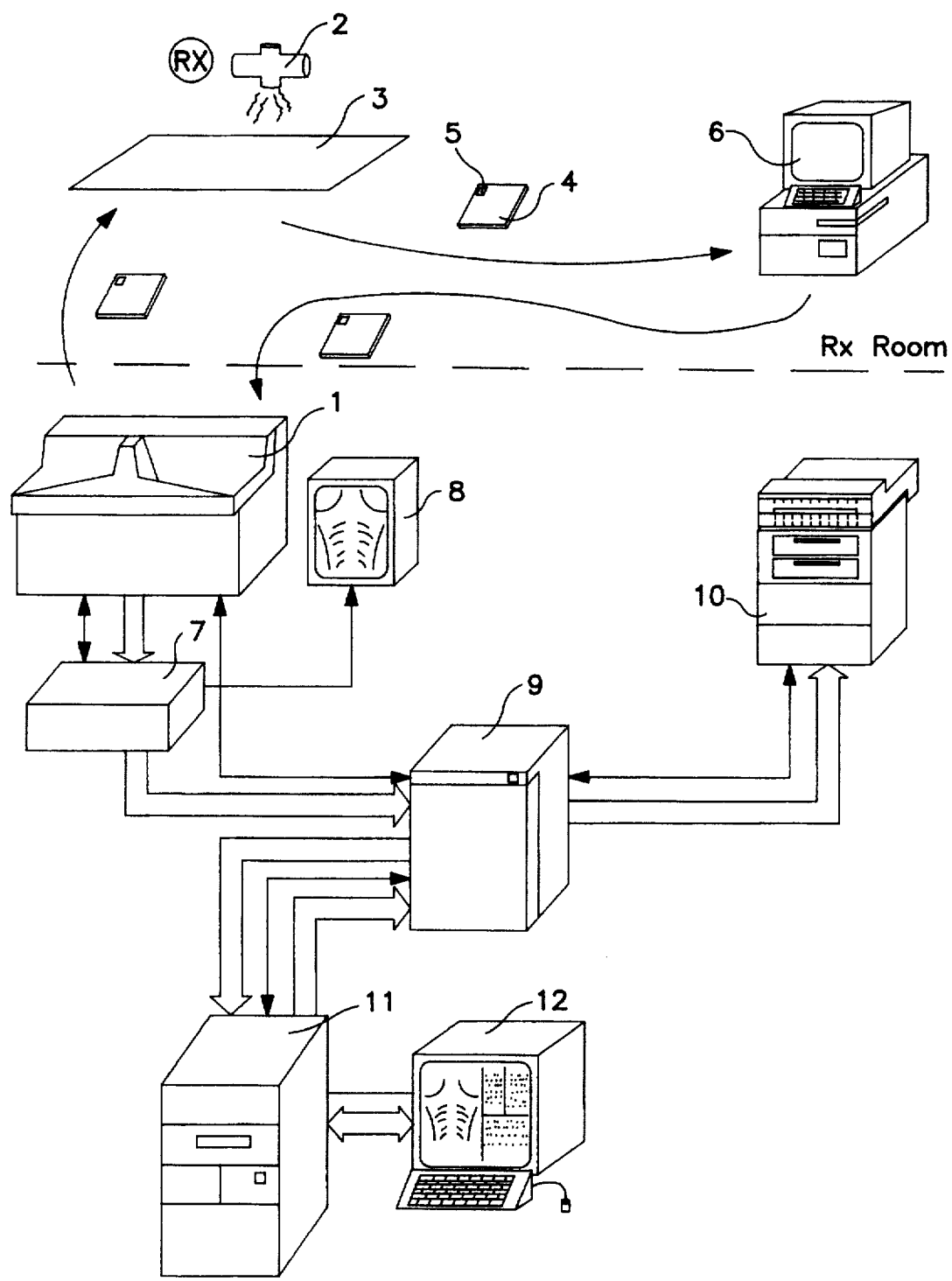
FIG. 1 is a general view of a system in which the method of the present invention can be applied.

A simplified block diagram of a system in which the method of the invention can be implemented is shown in FIG. 1.

A radiation image of an object was recorded on a photostimulable phosphor screen (3) by exposing (2) said screen to x-rays transmitted through the object (not shown). The stimulable phosphor screen was conveyed in a cassette (4) provided with an electrically erasable programmable read only memory (EEPROM) (5). In an identification station (6) various kinds of data, for example patient identification data (name, date of birth) and data relating to the exposure and/or to the signal processing such as processing parameters were written into the EEPROM (5).

Figure 2:
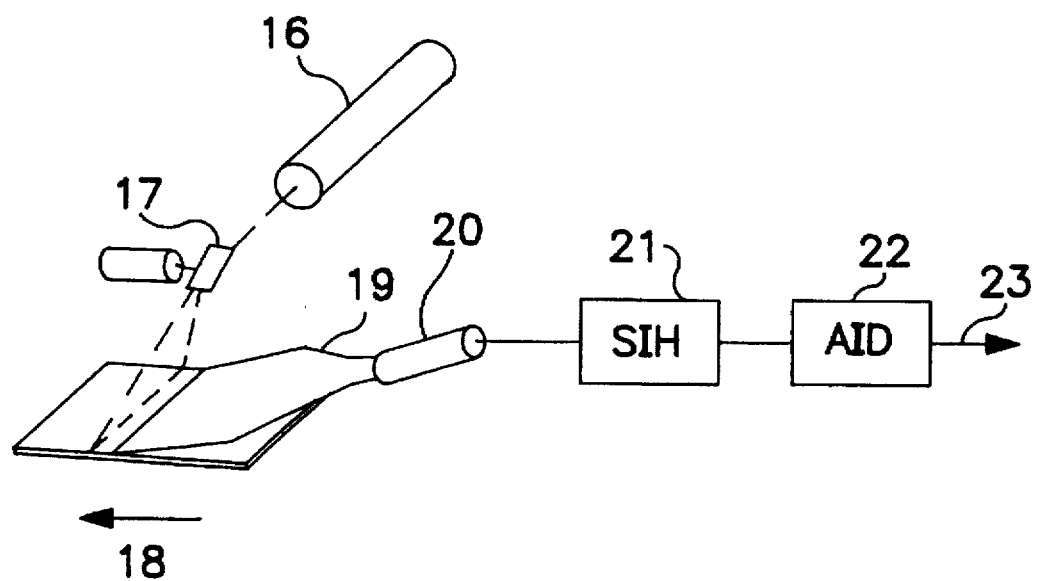
FIG. 2 is a detailed view of a system for reading an image stored in a photostimulable phosphor screen.

In a radiation image read-out apparatus (1) the information stored in the EEPROM and the image stored in the photostimulable phosphor screen were read-out. The read-out method is illustrated in FIG. 2. The stored image was read-out by scanning the phosphor screen with stimulating rays emitted by a laser 16. The stimulating rays were deflected into the main scanning direction by means of galvanometric deflection 17. The subscanning was performed by transporting the phosphor screen in the subscanning direction 18. The stimulated emission was directed by means of a light collector 19 onto a photomultiplier 20 for conversion into an electrical image representation. Next, the signal was sampled by a sample and hold circuit 21, and converted into a 12 bit signal by means of an analog to digital convertor 22. The digital image signal 23 was sent to the image processing module of the read-out apparatus (FIG. 1, numeral 7) where it was stored in an internal buffer.

The read-out signal was also applied to a preview monitor 8 for display immediately after read-out providing an operator with an early feed back on the performed exposure.

The read-out apparatus 1 and processing module 7 were further connected to a workstation 11 and associated review console 12 where off-line processing according to the present invention is performed.

The read-out apparatus and associated processor as well as the workstation and associated review console were connected via a buffer 9 to an output recorder 10.

In processing unit 7 the digital image signal was subjected to a decomposition into detail images at multiple resolution levels and a residual image. These detail images and residual image were then transmitted from the image processor to the image workstation 11, 12 via a digital communication channel where they were stored on hard disc. Alternatively archival on optical disc could be provided (not shown).

On-line processing generally comprises a modification of the detail images which may serve various purposes followed by a reconstruction of a processed image by applying an inverse transform to the modified detail images and the residual image, the reconstruction process being such that when it would have been applied to the unmodified detail images and the residual image this would have resulted in the original unprocessed image or a close approximation thereof.

The on-line processing was controlled with the aid of data indicative of specific processing procedures that were written into the EEPROM provided on the screen conveying cassette (cfr. numerals 4 and 5 in FIG. 1) in the identification station (numeral 6 in FIG. 1) in the form of a processing-identifier.

In the read-out apparatus 1 the information stored in the EEPROM was read-out and transmitted to the image processor 7 where the processing parameters corresponding with the read-out processing identifier were retrieved from a stored parameter table and applied when performing the effective processing.

Figure 3:
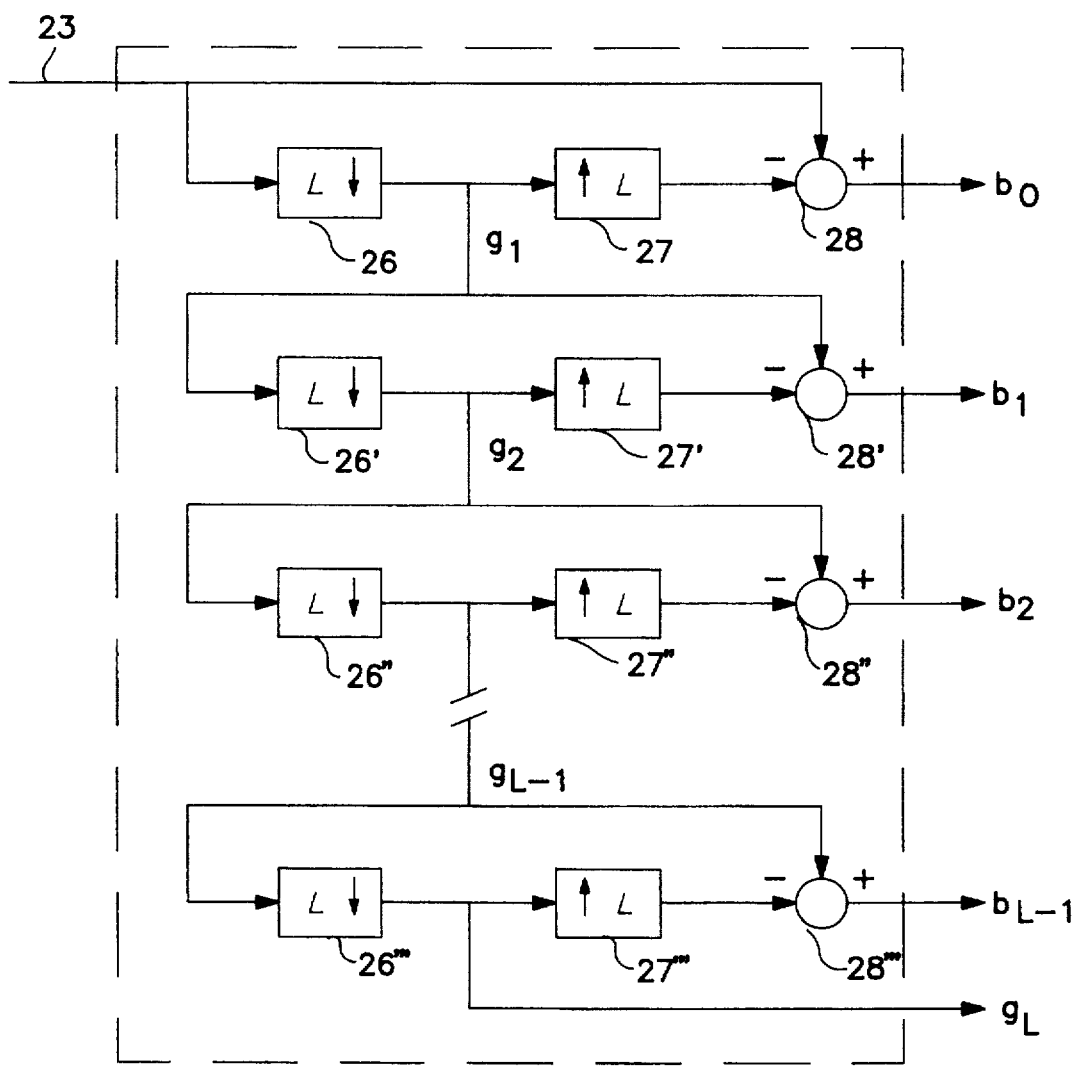
FIG. 3 illustrates a specific decomposition method.

One embodiment of a decomposition process is illustrated in FIG. 3. The original image signal 23 was filtered by means of a low pass filter 26, and subsampled by a factor of two, which is implemented by computing the resulting low pass image $g_1$ only at every other pixel position of every alternate row.

A detail image $b_0$ at the finest level is obtained by interpolating the low pass image $g_1$ while at the same time inserting an extra column and row every other column and row respectively, and pixelwise subtracting the interpolated image from the original image 23. The interpolation was effectuated by the interpolator 27, which inserts a column of zero values every other column, and a row of zero values every other row respectively, and next convolves the extended image with a low pass filter. The subtraction is done by the adder 28.

The same process is repeated on the low pass image $g_1$ instead of the original image 23, yielding a low pass image $g_1$ and a detail image $b_1$. A sequence of detail images $b_i$, i=0..L−1 and a residual low pass image g.L is obtained by iterating the above process L times.

The finest detail image $b_0$ has the same size as the original image. The next coarser detail image $b_1$ has only half as many rows and columns as the first detail image $b_0$. At each step of the iteration the characteristic spatial frequency of the resulting detail image is only half of that of the previous finer detail image, and also the number of columns and rows is halved, in accordance with the Nyquist criterion. After the last iteration a residual image $g_L$ is left which can be considered to be a very low resolution approximation of the original image. In the extreme case it consists of only 1 pixel which represents the average value of the original image 23.

The filter coefficients of the low pass filter 26 of the preferred embodiment are presented in FIG. 4. They correspond approximately to the samples of a two dimensional gaussian distribution on a 5×5 grid. The same filter coefficients are used for the low pass filters 26, 26', . . . 26''' at all scales. The same filter kernel with all coefficients multiplied by 4 is also used within the interpolators 27, 27', . . . 27'''. The factor of 4 compensates for the insertion of zero pixel columns and rows.

On-line processing further comprises the step of modifying for each image pixel values of said retrieved images to yield pixel values of a set of modified detail images. The modification depends on the specific objective envisioned by the processing, for example contrast enhancement, noise reduction etc.

In this particular embodiment contrast enhancing processing as well as noise suppression processing were performed.

These processing methods are described extensively in our copending European applications 91202079.9 filed 91.08.14 and U.S. Ser. No. 07/924,905 now U.S. Pat. No. 5,350,914 and in copending European application 92201802.3 filed 92.06.19.

After processing a processed image was reconstructed from the modified detail images and the residual image by applying a reconstruction algorithm.

Figure 5:
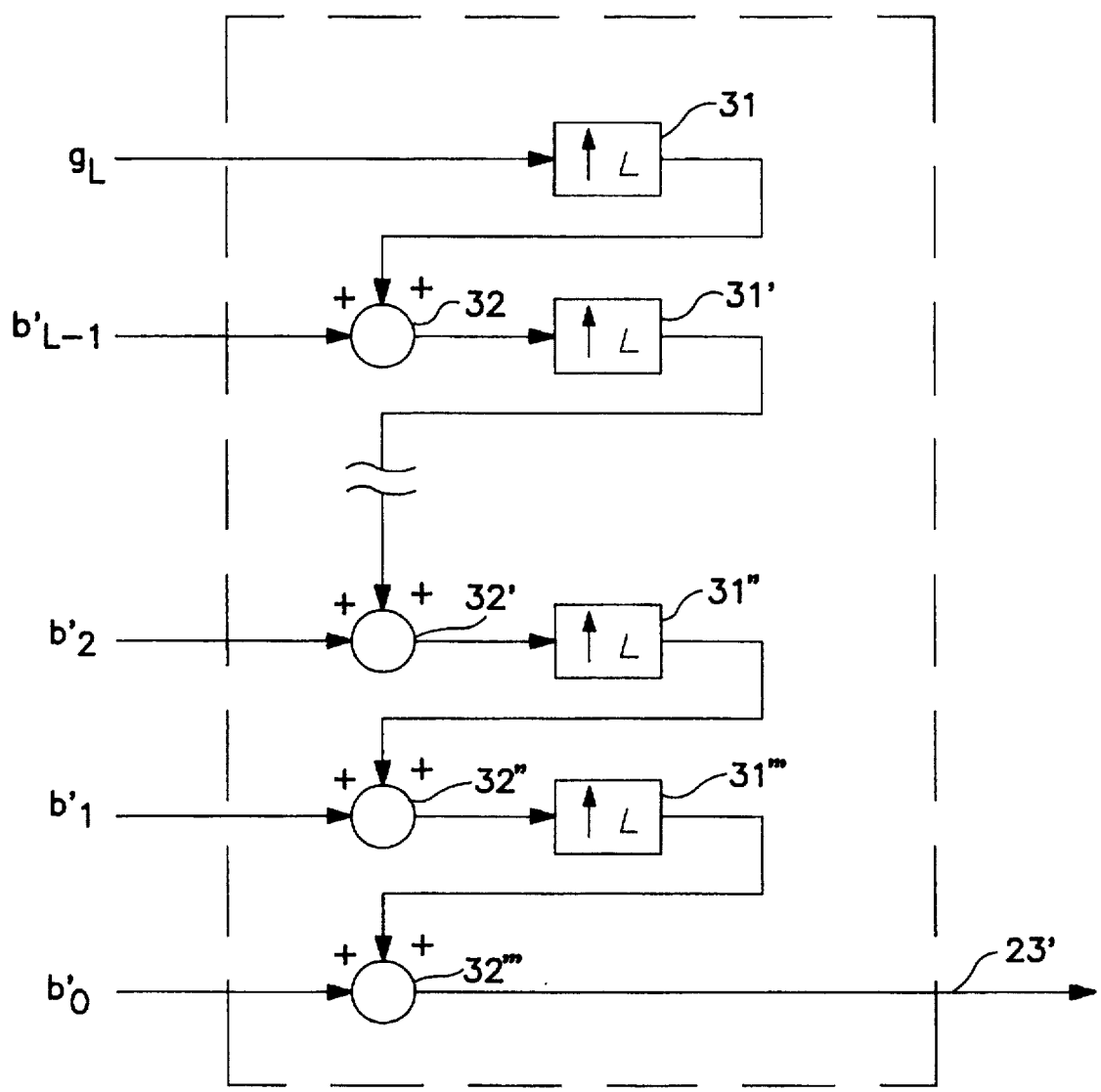
FIG. 5 illustrates a specific reconstruction process.

FIG. 5 is a scheme illustrating such a reconstruction algorithm.

The residual image $g_L$ is first interpolated by interpolator 31 to twice its original size and the interpolated image is next pixelwise added to the detail image of the coarsest level $b'_{L-1}$, using adder 32.

The resulting image is interpolated and added to the next finer detail image. When this process is iterated L times using the unmodified detail images $b_{L-1} \ldots b_0$ then the original image 23 will result. When at the other hand the detail images are modified before reconstruction according to the findings of the present invention, then a contrast enhanced image 23' will result. The interpolators 31, 31', 31" are identical to those used in the decomposition section.

The unmodified detail images and the residual image were also transmitted to the workstation (11, 12) where they were stored and kept available for off-line processing.

The off-line processing performed at the workstation was performed as described hereinafter.

First an image directory of a number of read out and stored images is displayed on the monitor screen. Composition of such an image directory is described extensively in our copending European application entitled "Method of displaying (a) radiographic image(s)" and filed on the even day.

Next one of the displayed images was selected for further interactive processing. Upon command, detail images pertaining to said selected image were retrieved from the disc of the workstation, however, only images up to a predetermined resolution level were retrieved. The predetermined resolution level was such that, when the retrieved detail images are modified and together with the residual image subjected to a reconstruction procedure, a reconstructed image results that has a resolution that is below the resolution of the display screen of the workstation.

The retrieved detail images were then subjected to an image processing algorithm wherein pixel values of the detail images were modified.

Then a reconstruction process were depicted in FIG. 5 was applied.

The resulting image after reconstruction was displayed on the monitor screen and was evaluated by a radiologist or an operator.

If the displayed image matched a standard set by this radiologist or operator the procedure was finished at this point. However, in case the displayed image did not match or when the operator would be interested in the result of an alternative processing, processing parameters were amended and the processing procedure was repeated taking into account the amended parameters on the original detail images that are for this purpose once again retrieved from the workstation disc or the detail images stored previously in working memory were used. However, the time-consuming decomposition procedure as described with reference to FIG. 3 needed not be repeated and processing and reconstruction could be performed on a subset of detail images and the residual image.

Selection of the different parameter settings for processing was performed with the aid of a graphic user interface provided on the workstation. This graphic interface provides via icons, menu's and tables selection of different preprogrammed sets of processing parameters dedicated to specific examination types or specific processing types.

At the point where a satisfactory processed image was obtained, the image processing was performed with the actual processing parameters not on a subset of the detail images but on the entire number of detail images and the reconstruction was performed with the residual image and all modified detail images.

The finally processed image was then sent to an output laser recorder for reproduction on film.

We claim:

1. A method of processing a digital signal representation of a radiographic image comprising the steps of:
   1) transforming said image into a decomposed image comprising a sequence of detail images at multiple resolution levels and a residual image, wherein the detail images at successively coarser resolution levels are obtained as the result of each of K iterations of the following steps:
      a) computing an approximation image at a next coarser level by applying a low pass filter to the approximation image corresponding to the current iteration, and subsampling the result in proportion to the reduction in spatial frequency bandwidth, using however the original image as input to said low pass filter in the course of the first iteration; and
      b) computing a detail image as the pixelwise difference between the approximation image corresponding to the current iteration and the approximation image at a next coarser resolution level computed according to step (a), both images being brought into register by proper interpolation of the latter image, and wherein the residual image is equal to the approximation image produced by the last iteration;
   2) storing said detail images and said residual image into a memory;
   3) retrieving from said memory detail images up to a predetermined resolution level among said multiple resolution levels, and said residual image;
   4) processing retrieved detail images in accordance with a set of processing parameters;
   5) generating a reconstructed image by applying the inverse of the decomposition transformation to the detail images processed in step 4 with the reconstructed image being the result of iterating K times the following procedure, starting from the coarsest processed detail image and the residual image, by computing an approximation image at a current resolution level by pixelwise adding a processed detail image at the same resolution level to the approximation image at a coarser resolution level corresponding to the previous iteration both images being brought into register by proper interpolation of the latter image, using said residual image instead of said coarser approximation image in the course of the first iteration;
   6) displaying said reconstructed image and evaluating it; and, 7) amending the numerical values of said processing parameters based on the result of the evaluation and repeating steps 3 to 6 until the result of the evaluation satisfies an operator.

2. A method according to claim 1 wherein at least a set of processing parameters leading to the evaluation that satisfies said operator is stored in a database.

3. Method according to claim 1 wherein the number of pixels in each detail image decreases at each coarser resolution level.

4. A method according to claim 1 wherein said radiographic image is stored in a photostimulable phosphor screen and wherein said digital image representation is obtained by scanning said screen with stimulating irradiation, detecting light emitted upon stimulation and converting said detected light into a digital signal representation.

* * * * *